(12) United States Patent
Kraemer

(10) Patent No.: US 11,026,726 B2
(45) Date of Patent: Jun. 8, 2021

(54) MINIMAL-PROFILE ANTERIOR CERVICAL PLATE AND CAGE APPARATUS AND METHOD OF USING SAME

(71) Applicant: K2M, Inc., Leesburg, VA (US)

(72) Inventor: Paul E. Kraemer, Westfield, IN (US)

(73) Assignee: K2M, Inc., Leesburg, VA (US)

( * ) Notice: Subject to any disclaimer, the term of this patent is extended or adjusted under 35 U.S.C. 154(b) by 66 days.

(21) Appl. No.: 16/132,800

(22) Filed: Sep. 17, 2018

(65) Prior Publication Data

US 2019/0015136 A1 Jan. 17, 2019

Related U.S. Application Data

(63) Continuation of application No. 13/932,676, filed on Jul. 1, 2013, now Pat. No. 10,076,364.

(60) Provisional application No. 61/665,934, filed on Jun. 29, 2012.

(51) Int. Cl.
*A61B 17/70* (2006.01)
*A61B 17/88* (2006.01)
*A61F 2/44* (2006.01)
*A61F 2/30* (2006.01)
*A61B 17/00* (2006.01)

(52) U.S. Cl.
CPC .......... *A61B 17/7059* (2013.01); *A61B 17/88* (2013.01); *A61F 2/4455* (2013.01); *A61B 2017/00261* (2013.01); *A61F 2/447* (2013.01); *A61F 2002/30331* (2013.01); *A61F 2002/30383* (2013.01); *A61F 2002/30578* (2013.01)

(58) Field of Classification Search
CPC .................................................. A61B 17/7059
See application file for complete search history.

(56) References Cited

U.S. PATENT DOCUMENTS

| | | | |
|---|---|---|---|
| 5,180,381 A | 1/1993 | Aust et al. | |
| 6,066,175 A | * 5/2000 | Henderson | ................ A61F 2/44 |
| | | | 623/17.11 |
| 6,113,637 A | 9/2000 | Gill et al. | |
| 6,152,927 A | 11/2000 | Farris et al. | |
| 6,156,037 A | 12/2000 | LeHuec et al. | |
| 6,193,721 B1 | 2/2001 | Michelson | |
| 6,293,949 B1 | 9/2001 | Justis et al. | |
| 6,364,880 B1 | 4/2002 | Michelson | |
| 6,454,769 B2 | 9/2002 | Wagner et al. | |
| 6,503,250 B2 | 1/2003 | Paul | |

(Continued)

FOREIGN PATENT DOCUMENTS

| | | |
|---|---|---|
| CA | 2437593 A1 | 8/2002 |
| FR | 2874316 A1 | 2/2006 |

(Continued)

*Primary Examiner* — Tessa M Matthews
(74) *Attorney, Agent, or Firm* — Lerner, David, Littenberg, Krumholz & Mentlik, LLP

(57) ABSTRACT

An apparatus and method for fusing cervical vertebrae is provided. The apparatus may include a plate configured to be affixed to at least two vertebrae, and at least two screws configured to affix the plate to an anterior surface of the at least two vertebrae, wherein when the plate is affixed to the at least two vertebrae, the plate is configured to be partially disposed in a disc space between the at least two vertebrae, and extend in an anterior direction beyond an anterior surface of the at least two vertebrae.

17 Claims, 16 Drawing Sheets

(56) References Cited

U.S. PATENT DOCUMENTS

| | | |
|---|---|---|
| 6,533,786 B1 | 3/2003 | Needham et al. |
| 6,890,335 B2 | 5/2005 | Grabowski et al. |
| 7,169,150 B2 | 1/2007 | Shipp et al. |
| 7,278,997 B1 | 10/2007 | Mueller et al. |
| 7,303,564 B2 | 12/2007 | Freid et al. |
| 7,500,976 B2 | 3/2009 | Suh |
| 7,625,375 B2 | 12/2009 | Garden et al. |
| 7,686,806 B2 | 3/2010 | Rhyne |
| 7,766,947 B2 | 8/2010 | Hawkes et al. |
| 7,815,681 B2 | 10/2010 | Ferguson |
| 7,857,839 B2 | 12/2010 | Duong et al. |
| 7,862,597 B2 | 1/2011 | Gause et al. |
| 8,043,346 B2 | 10/2011 | Markworth |
| 8,105,366 B2 | 1/2012 | Null et al. |
| 8,216,312 B2 | 7/2012 | Gray |
| 8,236,034 B2 | 8/2012 | Binder et al. |
| 8,361,126 B2 | 1/2013 | Perrow et al. |
| 8,403,969 B2 | 3/2013 | Wallenstein et al. |
| 8,403,970 B1 | 3/2013 | Bedor |
| 8,414,651 B2 | 4/2013 | Tyber et al. |
| 8,419,777 B2 | 4/2013 | Walker et al. |
| 8,486,115 B2 | 7/2013 | Fisher et al. |
| 8,500,782 B2 | 8/2013 | Kovach et al. |
| 8,500,811 B2 | 8/2013 | Blain et al. |
| 8,535,354 B2 | 9/2013 | Cummins |
| 8,641,765 B2 | 2/2014 | Muhanna |
| 8,690,948 B2 | 4/2014 | Armstrong et al. |
| 8,696,721 B2 | 4/2014 | Blain |
| 8,801,785 B2 | 8/2014 | Brittan et al. |
| 8,845,737 B2 | 9/2014 | Melkent et al. |
| 8,852,278 B2 | 10/2014 | Bellas |
| 8,900,277 B2 | 12/2014 | Perrow et al. |
| 8,945,226 B2 | 2/2015 | Johnston et al. |
| 8,945,227 B2 | 2/2015 | Kirschman |
| 8,956,415 B2 | 2/2015 | Cowan |
| 9,039,775 B2 | 5/2015 | Fraser et al. |
| 9,078,718 B2 | 7/2015 | Campbell |
| 9,078,765 B2 | 7/2015 | Louis et al. |
| 9,107,767 B2 | 8/2015 | Berger et al. |
| 9,180,022 B2 | 11/2015 | Georges et al. |
| 9,186,257 B2 | 11/2015 | Geisler et al. |
| 9,198,768 B1 | 12/2015 | Pisharodi |
| 9,220,547 B2 | 12/2015 | Blain et al. |
| 9,220,609 B2 * | 12/2015 | Mueller ............ A61B 17/7098 |
| 9,248,027 B2 | 2/2016 | Dunworth et al. |
| 9,248,028 B2 | 2/2016 | Gamache |
| 9,283,091 B2 | 3/2016 | Melkent et al. |
| 9,320,549 B2 | 4/2016 | Fraser et al. |
| 9,364,341 B2 | 6/2016 | Gowan |
| 9,364,342 B2 | 6/2016 | Walkenhorst et al. |
| 9,375,237 B2 | 6/2016 | Keegan et al. |
| 9,381,044 B2 | 7/2016 | Robinson et al. |
| 9,387,087 B2 | 7/2016 | Tyber |
| 9,427,330 B2 | 8/2016 | Petersheim et al. |
| 9,439,773 B2 | 9/2016 | Pisharodi |
| 9,603,611 B2 | 3/2017 | Perry |
| 9,603,718 B2 | 3/2017 | Cheng et al. |
| 9,615,733 B2 | 4/2017 | Nottmeier |
| 9,629,664 B2 | 4/2017 | Altarac et al. |
| 9,655,665 B2 | 5/2017 | Perrow |
| 9,662,821 B2 | 5/2017 | Clineff et al. |
| 9,730,804 B2 | 8/2017 | Cowan, Jr. et al. |
| 9,763,805 B2 | 9/2017 | Cheng et al. |
| 9,872,781 B2 | 1/2018 | Pavento |
| 2001/0020185 A1 | 9/2001 | Ray |
| 2002/0095155 A1 | 7/2002 | Michelson |
| 2002/0107571 A1 | 8/2002 | Foley |
| 2002/0107572 A1 | 8/2002 | Foley et al. |
| 2003/0167091 A1 | 9/2003 | Scharf |
| 2004/0002769 A1 | 1/2004 | Ferree |
| 2004/0039387 A1 | 2/2004 | Gause et al. |
| 2004/0098131 A1 | 5/2004 | Bryan et al. |
| 2004/0122426 A1 | 6/2004 | Michelson |
| 2004/0176777 A1 | 9/2004 | Zubok et al. |
| 2004/0181226 A1 | 9/2004 | Michelson |
| 2004/0193269 A1 | 9/2004 | Fraser et al. |
| 2004/0204712 A1 | 10/2004 | Kolb et al. |
| 2004/0210218 A1 | 10/2004 | Dixon et al. |
| 2004/0215195 A1 | 10/2004 | Shipp et al. |
| 2004/0220566 A1 | 11/2004 | Bray |
| 2004/0220571 A1 | 11/2004 | Assaker et al. |
| 2004/0249377 A1 * | 12/2004 | Kaes .................... A61F 2/28 606/247 |
| 2005/0033294 A1 | 2/2005 | Garden et al. |
| 2005/0049593 A1 | 3/2005 | Duong et al. |
| 2005/0049595 A1 | 3/2005 | Suh et al. |
| 2005/0071006 A1 | 3/2005 | Kirschman |
| 2005/0075633 A1 | 4/2005 | Ross |
| 2005/0085913 A1 * | 4/2005 | Fraser ............... A61B 17/7059 623/17.11 |
| 2005/0096657 A1 | 5/2005 | Autericque et al. |
| 2005/0101960 A1 | 5/2005 | Fiere et al. |
| 2005/0159813 A1 | 7/2005 | Molz |
| 2006/0036250 A1 | 2/2006 | Lange et al. |
| 2006/0074490 A1 | 4/2006 | Sweeney |
| 2006/0085071 A1 | 4/2006 | Lechmann et al. |
| 2006/0122603 A1 | 6/2006 | Kolb |
| 2006/0287653 A1 | 12/2006 | Rhyne |
| 2006/0293668 A1 | 12/2006 | May et al. |
| 2007/0050030 A1 | 3/2007 | Kim |
| 2007/0123884 A1 | 5/2007 | Abdou |
| 2007/0123987 A1 | 5/2007 | Bernstein |
| 2007/0173816 A1 | 7/2007 | Metz-Stavenhagen |
| 2007/0179504 A1 | 8/2007 | Kirschman |
| 2007/0270965 A1 | 11/2007 | Ferguson |
| 2007/0270968 A1 | 11/2007 | Baynham et al. |
| 2008/0021476 A1 | 1/2008 | Kirschman |
| 2008/0065070 A1 | 3/2008 | Freid et al. |
| 2008/0269806 A1 | 10/2008 | Zhang et al. |
| 2008/0294262 A1 | 11/2008 | Levieux |
| 2008/0312742 A1 | 12/2008 | Abernathie |
| 2009/0012529 A1 | 1/2009 | Blain et al. |
| 2009/0182430 A1 | 7/2009 | Tyber et al. |
| 2009/0210009 A1 | 8/2009 | Chao et al. |
| 2009/0287257 A1 | 11/2009 | Hagen |
| 2009/0326580 A1 | 12/2009 | Anderson et al. |
| 2010/0070037 A1 | 3/2010 | Parry |
| 2010/0137916 A1 | 6/2010 | Hynes et al. |
| 2010/0228297 A1 * | 9/2010 | Bray ................ A61B 17/7059 606/279 |
| 2010/0241231 A1 | 9/2010 | Marino et al. |
| 2010/0286781 A1 | 11/2010 | Bullard |
| 2010/0305704 A1 | 12/2010 | Messerli et al. |
| 2011/0040334 A1 | 2/2011 | Kaes et al. |
| 2011/0082550 A1 | 4/2011 | Yeh |
| 2011/0106159 A1 | 5/2011 | Nazeck |
| 2011/0144755 A1 | 6/2011 | Baynham et al. |
| 2011/0166658 A1 | 7/2011 | Garber |
| 2011/0270257 A1 | 11/2011 | Moore |
| 2011/0282392 A1 * | 11/2011 | Murphy ............ A61K 38/1841 606/279 |
| 2011/0288590 A1 | 11/2011 | O'Farrell et al. |
| 2012/0041559 A1 | 2/2012 | Melkent |
| 2012/0065688 A1 | 3/2012 | Nehls |
| 2012/0071933 A1 | 3/2012 | DeRidder |
| 2012/0078372 A1 | 3/2012 | Gamache et al. |
| 2012/0078373 A1 | 3/2012 | Gamache et al. |
| 2012/0172989 A1 | 7/2012 | McCarthy |
| 2012/0232599 A1 | 9/2012 | Schoenly et al. |
| 2012/0245690 A1 | 9/2012 | Cowan, Jr. |
| 2013/0053895 A1 | 2/2013 | Stoll et al. |
| 2013/0282127 A1 | 10/2013 | Gray |
| 2013/0345813 A1 | 12/2013 | Frank et al. |
| 2014/0005727 A1 | 1/2014 | Kraemer |
| 2014/0012318 A1 | 1/2014 | Goel |
| 2014/0012380 A1 | 1/2014 | Laurence et al. |
| 2014/0058446 A1 | 2/2014 | Bernstein |
| 2014/0107786 A1 | 4/2014 | Geisler et al. |
| 2014/0128924 A1 | 5/2014 | Perrow et al. |
| 2014/0200670 A1 | 7/2014 | Chin et al. |
| 2014/0228960 A1 | 8/2014 | Forterre et al. |
| 2014/0277505 A1 | 9/2014 | Mitchell |
| 2014/0336770 A1 | 11/2014 | Petersheim et al. |
| 2014/0371859 A1 | 12/2014 | Petersheim et al. |

(56) References Cited

U.S. PATENT DOCUMENTS

| | | |
|---|---|---|
| 2015/0025635 A1 | 1/2015 | Laubert |
| 2015/0032220 A1 | 1/2015 | Tyber et al. |
| 2015/0164651 A1 | 6/2015 | Zubok et al. |
| 2015/0230832 A1 | 8/2015 | Fraser et al. |
| 2015/0257796 A1 | 9/2015 | Baynham |
| 2015/0282940 A1 | 10/2015 | Baynham |
| 2015/0374510 A1 | 12/2015 | Fiechter et al. |
| 2016/0051373 A1 | 2/2016 | Faulhaber |
| 2016/0051374 A1 | 2/2016 | Faulhaber |
| 2016/0058480 A1 | 3/2016 | Laubert et al. |
| 2016/0081818 A1 | 3/2016 | Waugh et al. |
| 2016/0128844 A1 | 5/2016 | Tyber |
| 2016/0143746 A1 | 5/2016 | Robie et al. |
| 2016/0166404 A1 | 6/2016 | Faulhaber |
| 2016/0213405 A1 | 7/2016 | Moore et al. |
| 2016/0242925 A1 | 8/2016 | Terrell et al. |
| 2016/0242927 A1 | 8/2016 | Seifert et al. |
| 2016/0262905 A1 | 9/2016 | Prado et al. |
| 2016/0270928 A1 | 9/2016 | Yen |
| 2016/0296341 A1 | 10/2016 | Tatsumi |
| 2016/0367379 A1 | 12/2016 | Refai |
| 2017/0014239 A1 | 1/2017 | Seifert et al. |
| 2017/0014240 A1 | 1/2017 | Seifert et al. |
| 2017/0020679 A1 | 1/2017 | Maclennan |
| 2017/0020680 A1 | 1/2017 | Cheng et al. |
| 2017/0020685 A1 | 1/2017 | Geisler et al. |
| 2017/0049491 A1 | 2/2017 | Ross et al. |
| 2017/0049579 A1 | 2/2017 | Quinlan et al. |
| 2017/0095344 A1 | 4/2017 | Williams |
| 2017/0119537 A1 | 5/2017 | Tepper et al. |
| 2017/0172755 A1 | 6/2017 | Suh et al. |
| 2017/0172756 A1 | 6/2017 | Faulhaber |
| 2017/0181781 A1 | 6/2017 | Dubois et al. |
| 2017/0189077 A1 | 7/2017 | Blain |
| 2017/0202678 A1 | 7/2017 | Duffield et al. |
| 2017/0224388 A1 | 8/2017 | Walker et al. |
| 2017/0224389 A1 | 8/2017 | Tatsumi |
| 2017/0232147 A1 | 8/2017 | Clineff et al. |
| 2017/0238974 A1 | 8/2017 | Konieczynski et al. |
| 2018/0008419 A1 | 1/2018 | Tyber et al. |
| 2018/0036136 A1 | 2/2018 | Duffield et al. |

FOREIGN PATENT DOCUMENTS

| | | |
|---|---|---|
| FR | 2944692 A1 | 10/2010 |
| WO | 2013134210 A1 | 9/2013 |
| WO | 2015054066 A1 | 4/2015 |
| WO | 2016149141 A1 | 9/2016 |

\* cited by examiner

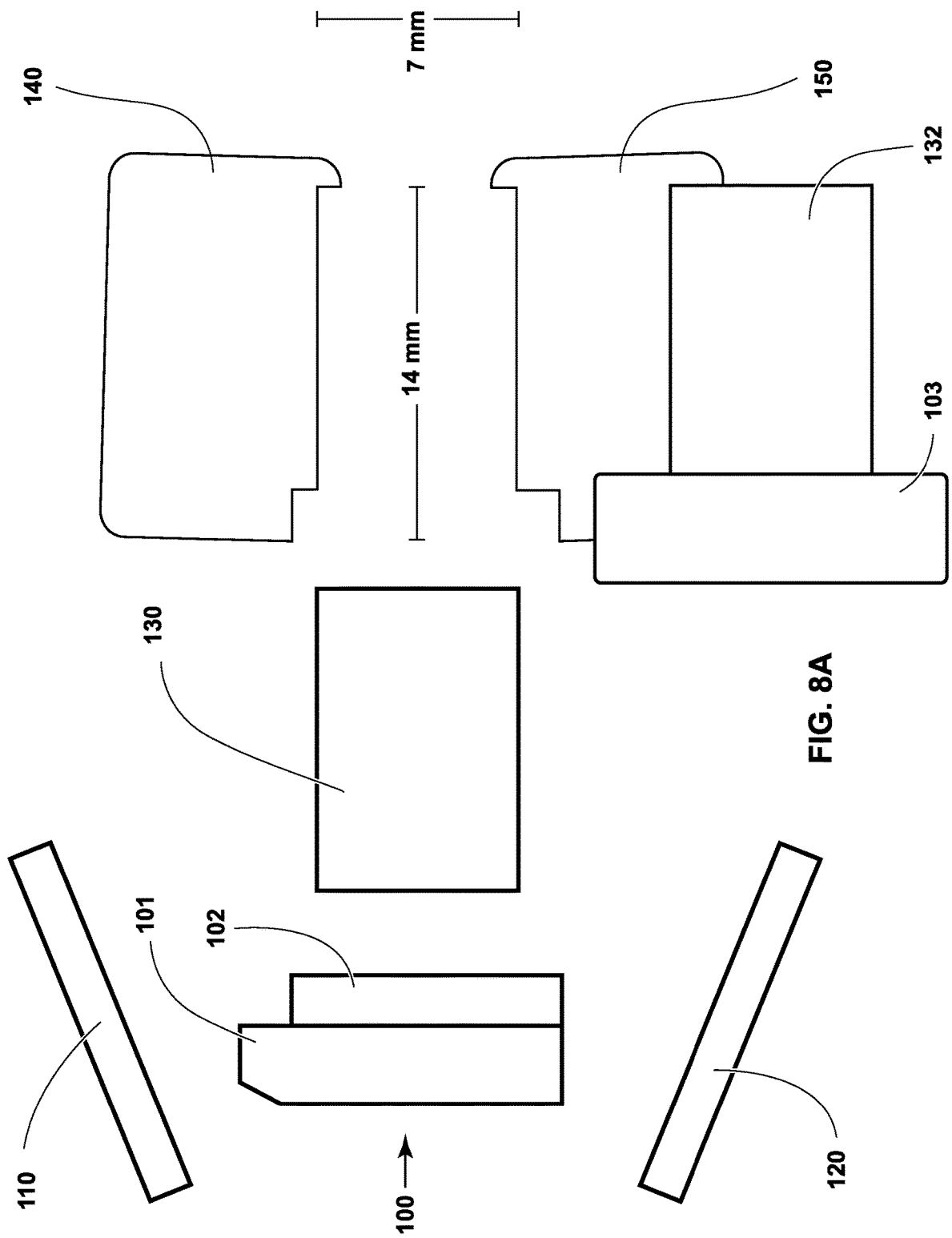

MINIMAL-PROFILE ANTERIOR CERVICAL PLATE AND CAGE APPARATUS AND METHOD OF USING SAME

CROSS-REFERENCE TO RELATED APPLICATIONS

This application claims priority to U.S. patent application Ser. No. 13/932,676, filed on Jul. 1, 2013, now U.S. Pat. No. 10,076,364, which claims priority to, and the benefit of, U.S. Provisional Patent Application Ser. No. 61/665,934 filed on Jun. 29, 2012, the contents of each of these prior applications are incorporated herein by reference in their entirety.

RELATED ART

Methods and apparatuses consistent with the exemplary embodiments relate to anterior cervical fusion. In particular, the exemplary embodiments relate to an apparatus and method for fusing cervical vertebrae wherein the apparatus secures a graft between vertebrae such that at least a portion of the apparatus extends beyond an anterior face of the vertebrae.

Anterior cervical discectomy and fusion (ACDF) is a procedure commonly used to treat cervical disc herniation. During the procedure, a surgeon removes the herniated disc from in between two vertebrae, and the two vertebrae above and below the disc space are fused together. To facilitate fusion and prevent the vertebrae from collapsing, the open disc space is filled with a bone graft. The bone graft and the vertebrae may be immobilized and held together with a metal plate and screws, which allows the bone graft to eventually join the vertebrae above and below the disc space to form one solid piece of bone. The manner in which the plate and screws are fixed to the vertebrae affect the healing process, and specifically fusing the vertebrae optimally, reproducibly, and with minimal disruption to native tissue.

SUMMARY

Accordingly, there is a need for an improved apparatus and method for facilitating anterior cervical fusion.

According to an aspect of one or more exemplary embodiments, there is provided an apparatus for fusing vertebrae after an anterior cervical discectomy. The apparatus according to one or more exemplary embodiments may include a plate configured to be affixed to an anterior surface of the at least two vertebrae, and at least two screws configured to affix the plate to an anterior surface of the at least two vertebrae. When the plate is affixed to the at least two vertebrae, the plate may extend in an anterior direction beyond the anterior surface of the at least two vertebrae, and may be partially disposed between the at least two vertebrae.

By positioning the plate such that it extends beyond the anterior surface of the two vertebrae, more room is available in the disc space for the bone graft to facilitate fusion. In other words, the surface area of the bone graft is maximized. By contrast, a "zero-profile" apparatus may include a plate that is disposed entirely within the disc space such that the plate does not extend beyond the anterior surface of the vertebrae. Disposing the plate within the disc space reduces the amount of space available for the bone graft, which may hinder vertebrae fusion.

In addition, by partially disposing the plate within the disc space and allowing the plate to extend beyond the anterior surface of the vertebrae, a shorter plate may be used so that a greater distance from the adjacent disc is maintained. If a plate is disposed entirely on the anterior surface of the vertebrae, the plate must be longer in order to accommodate the screws. Using a longer plate, however, reduces the distance between the plate and the adjacent disc, which may be problematic. Thus, by disposing the plate partially within the disc space and partially on the anterior surface of the vertebrae, there is a reduced risk that the plate will negatively affect the adjacent disc. In this configuration the screws may be inserted into the vertebrae at an angle, which is less prone to pullout as compared to horizontal screws.

The plate may extend 3 mm or less in an anterior direction beyond the anterior surface of the at least two vertebrae. The plate and the screws may be disposed such that there is at least 5 mm between the plate and an adjacent disc space.

The apparatus may also include a graft configured to be disposed between the at least two vertebrae. The graft may extend approximately 11 mm to 14 mm in a posterior direction from the anterior surface of the at least two vertebrae. The graft may include structural allograft bone, or a polyether ether ketone (PEEK) cage filled with allograft bone.

The plate may extend approximately 14 mm in a cephalo-caudal direction that is parallel to the anterior surface of the at least two vertebrae. The plate may include an anterior portion that extends in an anterior direction beyond the anterior surface of the at least two vertebrae, and a posterior portion configured to be detachably connected to the anterior portion. The anterior portion of the plate may include two recesses, and the posterior portion may include two anterior protrusions. The two recesses of the anterior portion may receive the two anterior protrusions of the posterior portion. The two anterior protrusions may be hollow, and configured to receive screws for affixing the plate to the vertebrae. The anterior portion may be made of titanium or other metal, and the posterior portion may be made of PEEK or other non-metal sub stance.

The posterior portion may extend approximately 2 mm in a posterior direction from the anterior surface of the at least two vertebrae, and the graft may extend approximately 12 mm in a posterior direction from the posterior portion of the plate. The posterior portion may extend approximately 10 mm in the cephalo-caudal direction. These dimensions are merely exemplary and one skilled in the art would understand that the dimensions may vary without departing from the inventive concept.

The apparatus may also include a third screw that is configured to fix the plate to the anterior surface of the at least two vertebrae. The third screw may be disposed between the at least two screws.

According to another aspect of one or more exemplary embodiments, there is provided a method for affixing a plate to at least one vertebrate to facilitate fusion after an anterior cervical discectomy. The method according to one or more exemplary embodiments may include carving a channel between the two vertebrae, inserting a graft into the channel, and affixing a plate to the two vertebrae such that a portion of the plate is within the channel and a portion of the plate extends in an anterior direction beyond an anterior surface of the two vertebrae.

The channel may have a posterior portion and an anterior portion. The cephalo-caudal height of the anterior portion may be greater than the cephalo-caudal height of the posterior portion. The posterior depth of the posterior portion may be greater than a posterior depth of the anterior portion. The channel may be carved with a cylindrical burr or router type device. The cylindrical burr may be a two-diameter reamer having a minor diameter channel for the bone graft and a major diameter for the plate. The diameter sizes may be chosen based on the patient's anatomy and/or the size of the plate and graft.

The plate may be affixed to the two vertebrae such that the plate is at least approximately 5 mm from a nearest disc in the cephalad and/or caudal direction.

The graft may extend approximately 11 mm to 14 mm in a posterior direction from the anterior surface of the two vertebrae.

BRIEF DESCRIPTION OF THE DRAWINGS

FIGS. 8A-E are exploded views of a fusion apparatus according to another exemplary embodiment as the apparatus is affixed to the vertebrae.

DETAILED DESCRIPTION OF EXEMPLARY EMBODIMENTS

Figure 1:
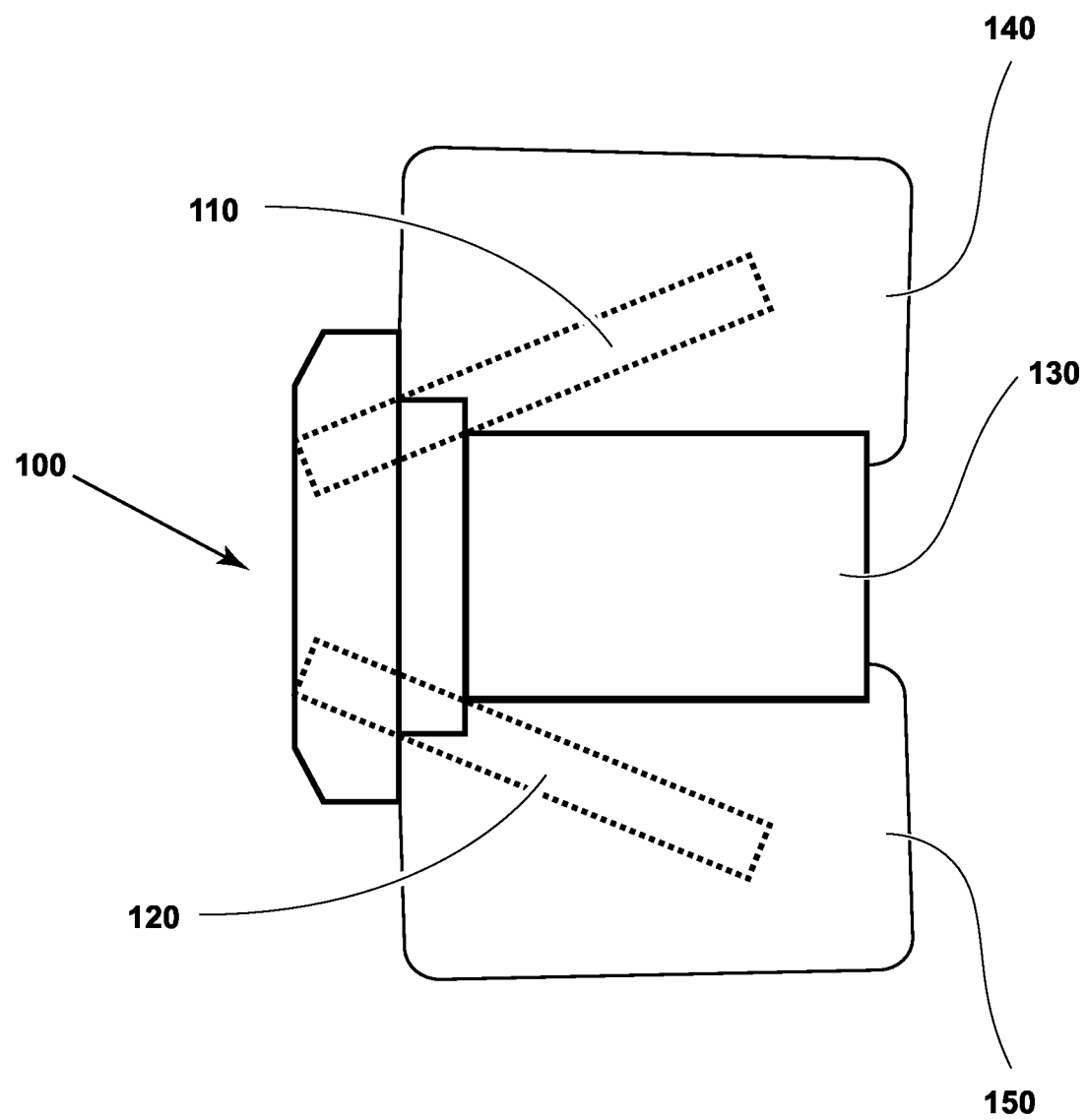
FIG. 1 is a lateral view of a fusion apparatus according an exemplary embodiment.

Reference will now be made in detail to the following exemplary embodiments, which are illustrated in the accompanying drawings, wherein like reference numerals refer to like elements throughout.

The exemplary embodiments may be embodied in various forms without being limited to the exemplary embodiments set forth herein. Descriptions of well-known parts are omitted for clarity.

FIG. 1 is a lateral view of a fusion apparatus for fusing two vertebrae according to an exemplary embodiment. The apparatus according to an exemplary embodiment may include a plate 100, screws 110 and 120, and graft 130. The apparatus may be used to fuse vertebrae 140 and 150 by securing graft 130 in the disc space between vertebrae 140 and 150.

After the disc is removed from the disc space, a reamer may be used to carve out a channel between the vertebrae 140 and 150. Graft 130 may then be inserted into the carved channel between the vertebrae 140 and 150. Plate 100 is then secured to vertebrae 140 and 150 using screws 110 and 120. Plate 100 may cover an anterior gap between vertebrae 140 and 150, such that a first portion of plate 100 is disposed within the channel between vertebrae 140 and 150, and a second portion of plate 100 is disposed beyond an anterior surface 160 of the vertebrae 140 and 150. More specifically, plate 100 may extend in an anterior direction beyond the anterior surface 160 of vertebrae 140 and 150 by up to approximately 3 mm. Plate 100 may also be disposed at least 5 mm from an adjacent disc space. For example, plate 100 may be at least 5 mm from the disc space (not shown) above vertebrate 140. Plate 100 may also be at least 5 mm from both disc spaces that are adjacent to disc space 130. In other words, plate 100 may be at least 5 mm from the disc space above vertebrate 140, and at least 5 mm from the disc space below vertebrate 150.

By disposing the plate 100 on the anterior surface 160 of vertebrae 140 and 150, as opposed to within the disc space between vertebrae 140 and 150, the surface area of graft 130 is maximized, thus increasing the fusion rate. For example, the graft 130 may extend approximately 11 mm to 14 mm in a posterior direction from the anterior surface 160 of vertebrae 140 and 150. In addition, by disposing the plate 100 partially within the channel between vertebrae 140 and 150, as opposed to entirely on the anterior surface 160, a shorter plate 100 may be used in order to increase the distance between the plate 100 and adjacent discs. The increased distance to the adjacent discs may reduce the risk of damaging the adjacent discs.

Moreover, by disposing the plate 100 on the anterior surface 160 of vertebrae 140 and 150, screws 110 and 120 are able to be inserted in a more anterior-posterior direction, as compared to zero-profile plates, which require that screws are inserted in a more cephalo-caudal direction. Inserting the screws in a more anterior-posterior direction makes it easier for the surgeon to insert the screws. On the other hand, plates disposed entirely on the anterior surface of the vertebrae are affixed using screws inserted in the anterior-posterior direction. Inserting the screws at an angle, as shown in the exemplary embodiment of FIG. 1, may reduce the possibility that the screws will pull out of the vertebrae.

Figure 2:
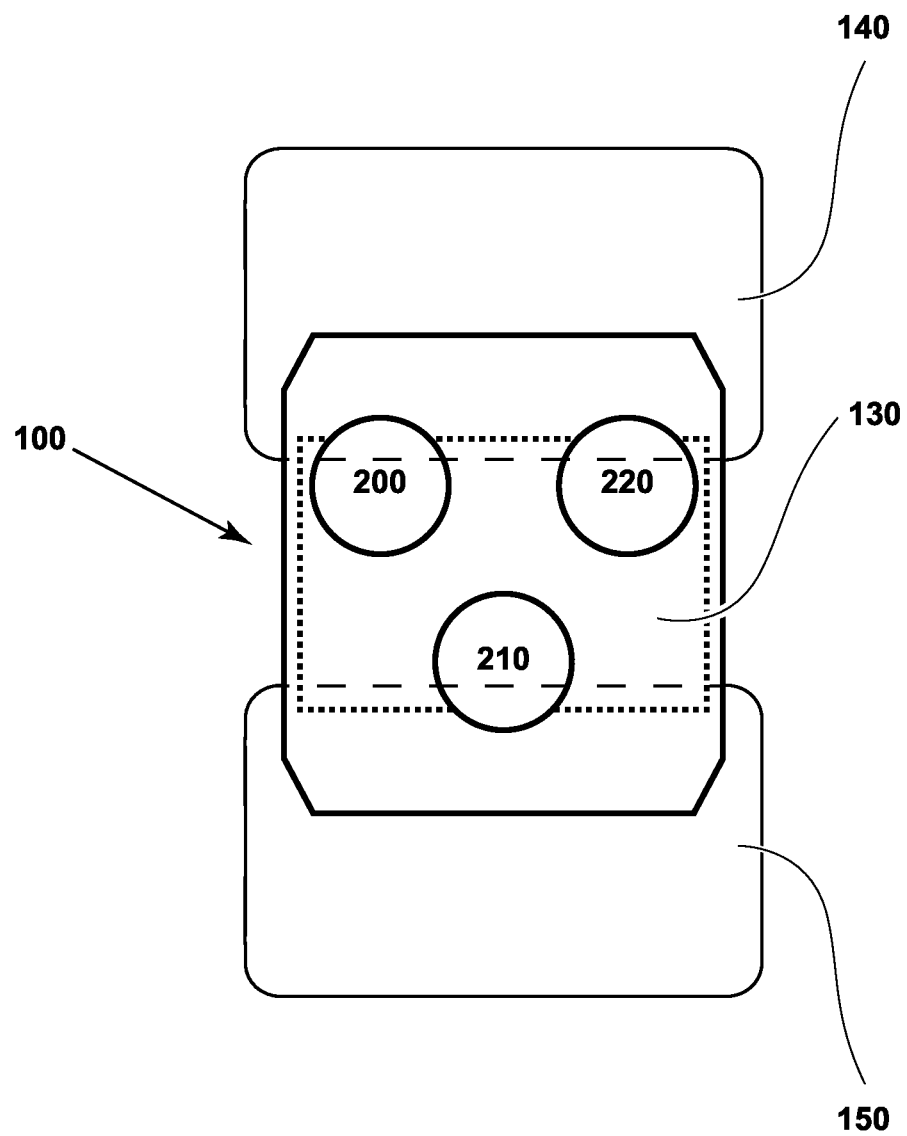
FIG. 2 is an anterior view of a fusion apparatus according to an exemplary embodiment.

FIG. 2 is an anterior view of a fusion apparatus for fusing two vertebrae according to an exemplary embodiment. In the exemplary embodiment of FIG. 2, three screws 200, 210, and 220 may be used to secure plate 100 to vertebrae 140 and 150. Screws 200 and 220 may screw into vertebrate 140 and screw 210 may screw into vertebrate 150. Screw 210 may be located between screws 200 and 220. Alternatively, according to another exemplary embodiment, a fourth screw (not shown) may be used to secure plate 100 to vertebrae 140 and 150. The fourth screw may be disposed such that two screws extend into vertebrate 140 and two screws extend into vertebrate 150. Of course, the ordinarily skilled artisan will appreciate from the instant disclosure that any number of screws in either or both of vertebrae 140 and 150 can be used without departing from the spirit and scope of the present teachings.

Figure 3:
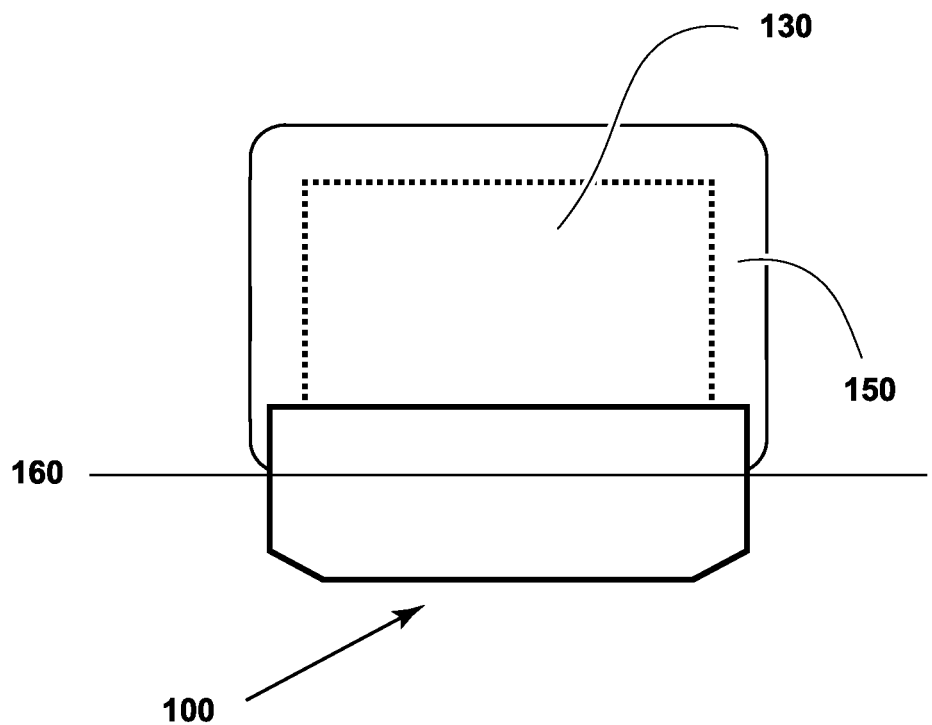
FIG. 3 is a cross-sectional view from the top of the spine of a fusion apparatus according to an exemplary embodiment.

FIG. 3 is a cross-sectional view of a fusion apparatus for fusing two vertebrae according to an exemplary embodiment. In the exemplary embodiment of FIG. 3, plate 100 may extend in the anterior direction beyond the anterior surface 160 of vertebrae 150. The plate 100 may also extend into the disc space where graft 130 is located. Graft 130 may extend in the posterior direction from plate 100 to substantially fill the remaining disc space. For example, graft 130 may extend approximately 11 mm to approximately 14 mm in the posterior direction. By allowing part of plate 100 to protrude from the anterior surface of the vertebrae, the surface area of the graft 130 may be increased.

Figure 4:
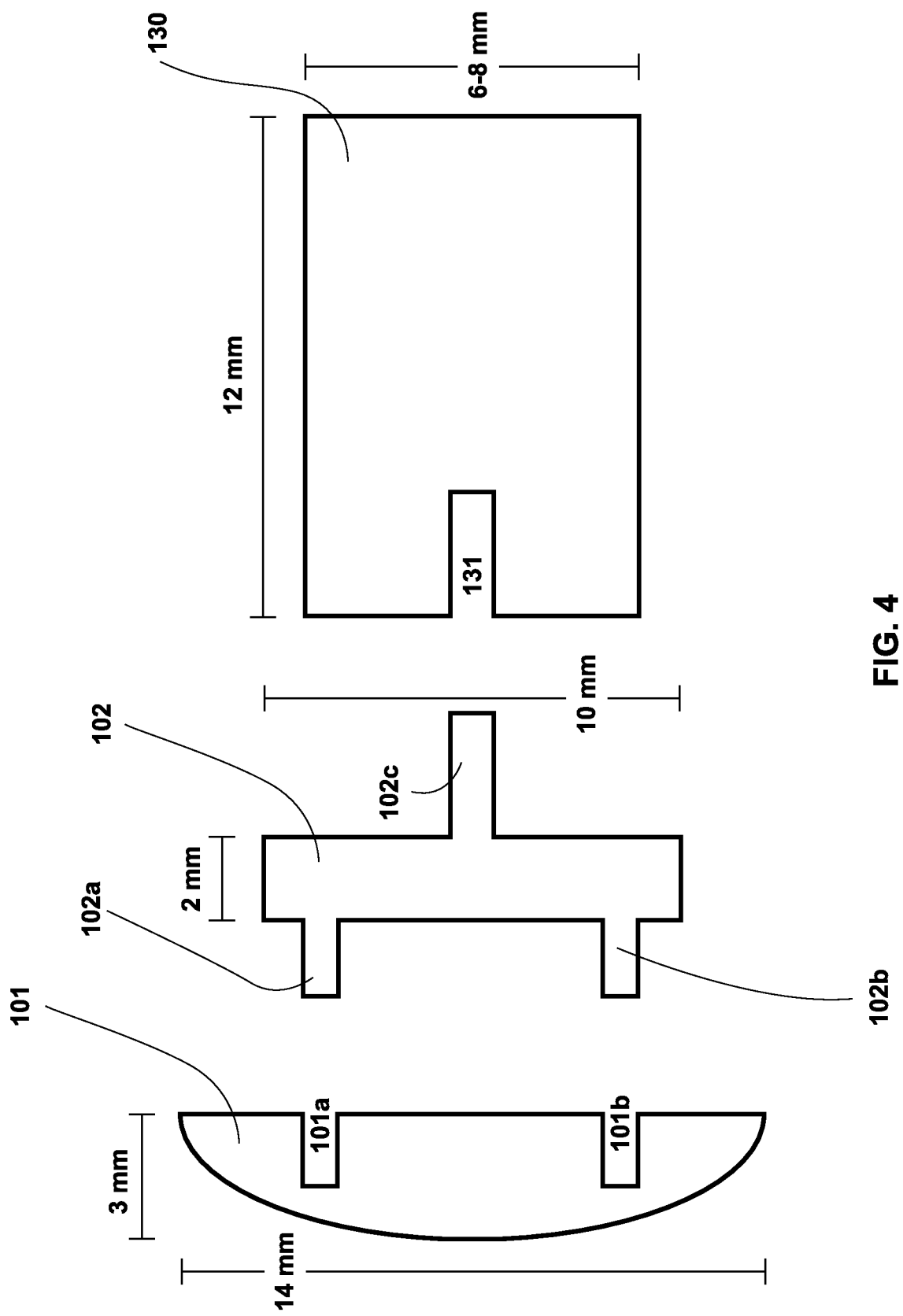
FIG. 4 is an exploded view of a fusion apparatus according to an exemplary embodiment.

FIG. 4 is an exploded view of a fusion apparatus for fusing two vertebrae according to an exemplary embodiment. In the exemplary embodiment of FIG. 4, the plate may include an anterior portion 101 and a posterior portion 102. Anterior portion 101 may include a first recess 101a and a second recess 101b. Posterior portion 102 may include a first protrusion 102a, a second protrusion 102b, and a third protrusion 102c. First protrusion 102a and second protrusion 102b may extend in the anterior direction toward the anterior portion 101 of plate 100. First recess 101a and second recess 101*b* may receive first protrusion 102*a* and second protrusion 102*b*, respectively. First protrusion 102*a* and second protrusion 102*b* may be hollow in order to receive screws that affix the plate 100 to vertebrae 140 and 150. Third protrusion 102*c* may extend in the posterior direction toward the graft 130, which may include a graft recess 131 to receive the third protrusion 102*c*. The third protrusion 102*c* may be in the form of an arrowhead or other shape that connects the posterior portion 102 to graft 130. Alternatively, posterior portion 102 may not include a third protrusion 102*c*, and graft 130 may not include graft recess 131, so that plate 100 is not affixed to graft 130. In addition, anterior portion 101 and posterior portion 102 may be integral such that they form one solid plate.

According to an exemplary embodiment, anterior portion 101 may be approximately 14 mm long in the cephalo-caudal direction and approximately 3 mm deep in the anterior-posterior direction. Posterior portion 102 may be approximately 10 mm long in the cephalo-caudal direction and approximately 2 mm deep in the anterior-posterior direction. Graft 130 may be approximately 6 mm to 8 mm long in the cephalo-caudal direction, and approximately 12 mm deep in the anterior-posterior direction.

According to an exemplary embodiment, anterior portion 101 may be made of titanium or another metallic material. Posterior portion 102 may be made of polyether ether ketone (PEEK) or another non-metal material. Alternatively, according to another exemplary embodiment, anterior portion 101 may be made of PEEK or another non-metal material, and posterior portion 102 may be made of titanium or another metallic material. According to yet another exemplary embodiment, anterior portion 101 and posterior portion 102 may be made of titanium or another metallic material. Graft 130 may be made of bone, which may come from the patient or may be a cadaveric bone. Graft 130 may also be made of man-made plastic or ceramic material that may be packed with living bone tissue taken from the patient's spine during surgery.

Figure 5:
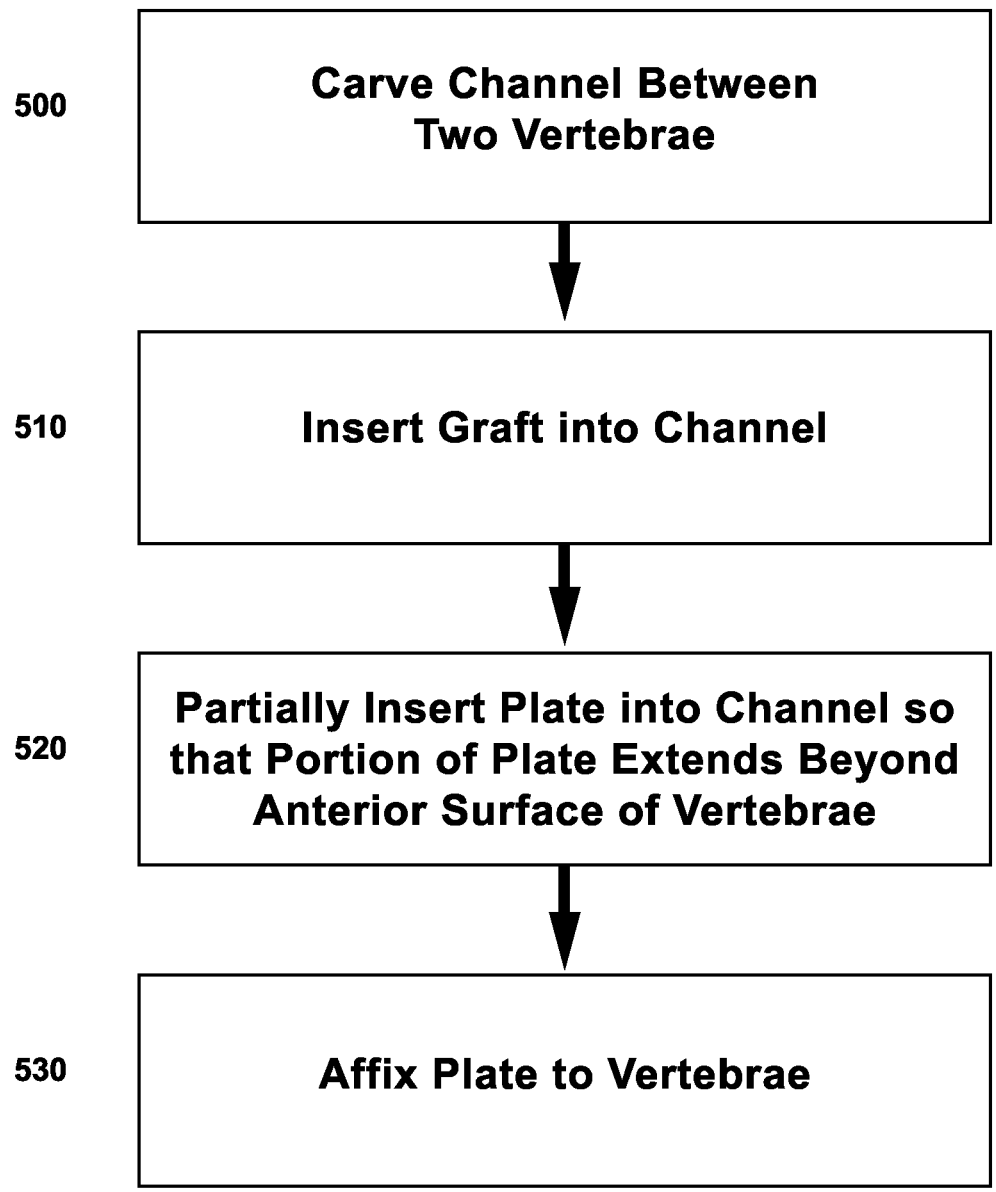
FIG. 5 is a flowchart of a method for fusing two vertebrae according to an exemplary embodiment.
Figure 6:
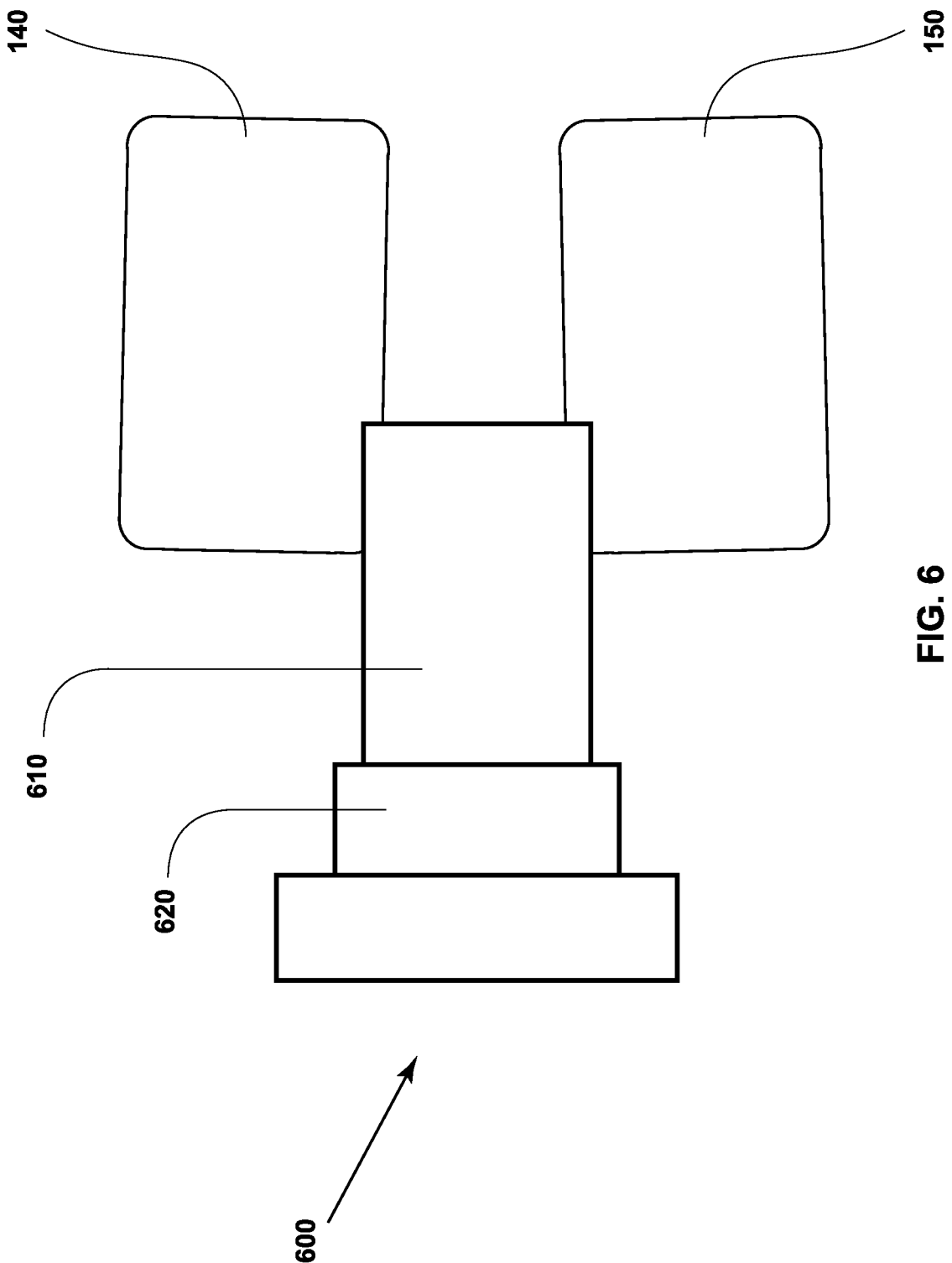
FIG. 6 is a side view of a reamer that may be used in a method for using fusing two vertebrae according to an exemplary embodiment.

FIG. 5 is a flowchart of a method for fusing two vertebrae according to an exemplary embodiment. FIG. 6 is a side view of a reamer that may be used in the method of FIG. 5. Referring to FIG. 5, the method of the exemplary embodiment begins at step 500 in which a channel is carved between two vertebrae. The reamer shown in FIG. 6 may be used to perform the carving step 500 of FIG. 5.

Referring to FIG. 6, reamer 600 may include a posterior portion 610 and an anterior portion 620. According to an exemplary embodiment, the cephalo-caudal height of the anterior portion 620 may be greater than the cephalo-caudal height of the posterior portion 610. For example, the anterior portion 620 may be approximately 10 mm long in the cephalo-caudal direction, and posterior portion 610 may be approximately 6 mm to approximately 8 mm long in the cephalo-caudal direction. In addition, anterior portion 620 may have a shorter anterior-posterior depth as compared to the anterior-posterior depth of posterior portion 610. For example, anterior portion 620 may have a depth of approximately 2 mm, and posterior portion 610 may have a depth of approximately 12 mm.

As the reamer 600 is inserted between vertebrae 140 and 150, the posterior portion 610 carves out a channel between the vertebrae 140 and 150. As the reamer 600 is inserted further, anterior portion 620 carves out a wider channel, such that a posterior end of the channel has a smaller cephalo-caudal height than an anterior end of the channel.

The dimensions of the reamer 600, and the other components, described herein are merely exemplary, and may vary. For example, the cephalo-caudal height of posterior portion 610 and anterior portion 620 may be set to correspond to the size of the graft and the size of the plate, respectively, to be inserted in the channel created by reamer 600. The cephalo-caudal height of posterior portion 610 and the cephalo-caudal height of the graft may vary, for example, in 1 mm or 0.5 mm increments. In addition, the cephalo-caudal height of the anterior portion 610 and the cephalo-caudal height of the plate may vary, for example, in 1 mm or 0.5 mm increments. According to an exemplary embodiment, the cephalo-caudal height of the anterior portion 610 and the cephalo-caudal height of the plate may be selected so that the plate is partially recessed into the anterior end of the channel when the plate is affixed to the vertebrae.

Referring to FIG. 5, in step 510, a graft is inserted into the channel carved in step 500. Graft 130 may be made of bone, which may come from the patient or may be a cadaveric bone. Graft 130 may also be made of man-made plastic or ceramic material that may be packed with living bone tissue taken from the patient's spine during surgery.

In step 520, a plate is partially inserted into the channel carved in step 500, so that a portion of the plate extends in the anterior direction beyond the anterior surface of the vertebrae. For example, the plate may extend approximately 2 mm into the channel, and may extend approximately 3 mm in the anterior direction beyond the anterior surface of the vertebrae.

In step 530, the plate is affixed to the vertebrae using two or more screws. According to an exemplary embodiment, three screws may be used to affix the plate, with first and second screws being screwed into the top vertebrate, and a third screw screwed into the bottom vertebrate. In this exemplary configuration, the third screw may be disposed horizontally (i.e., left-right on the patient's body) between the first and second screws. Alternatively, the first and second screws may be screwed into the bottom vertebrate, and the third screw may be screwed into the top vertebrate. In this exemplary configuration, the third screw may be disposed horizontally between the first and second screws. According to yet another embodiment, four screws may be used to affix the plate to the vertebrae in step 530. In this exemplary configuration, two screws may be screwed into each of the top vertebrate and bottom vertebrate. According to still another exemplary embodiment, two screws may be used to affix the plate to the vertebrae, with one screw being screwed into each of the top vertebrate and bottom vertebrate.

Figure 7A:
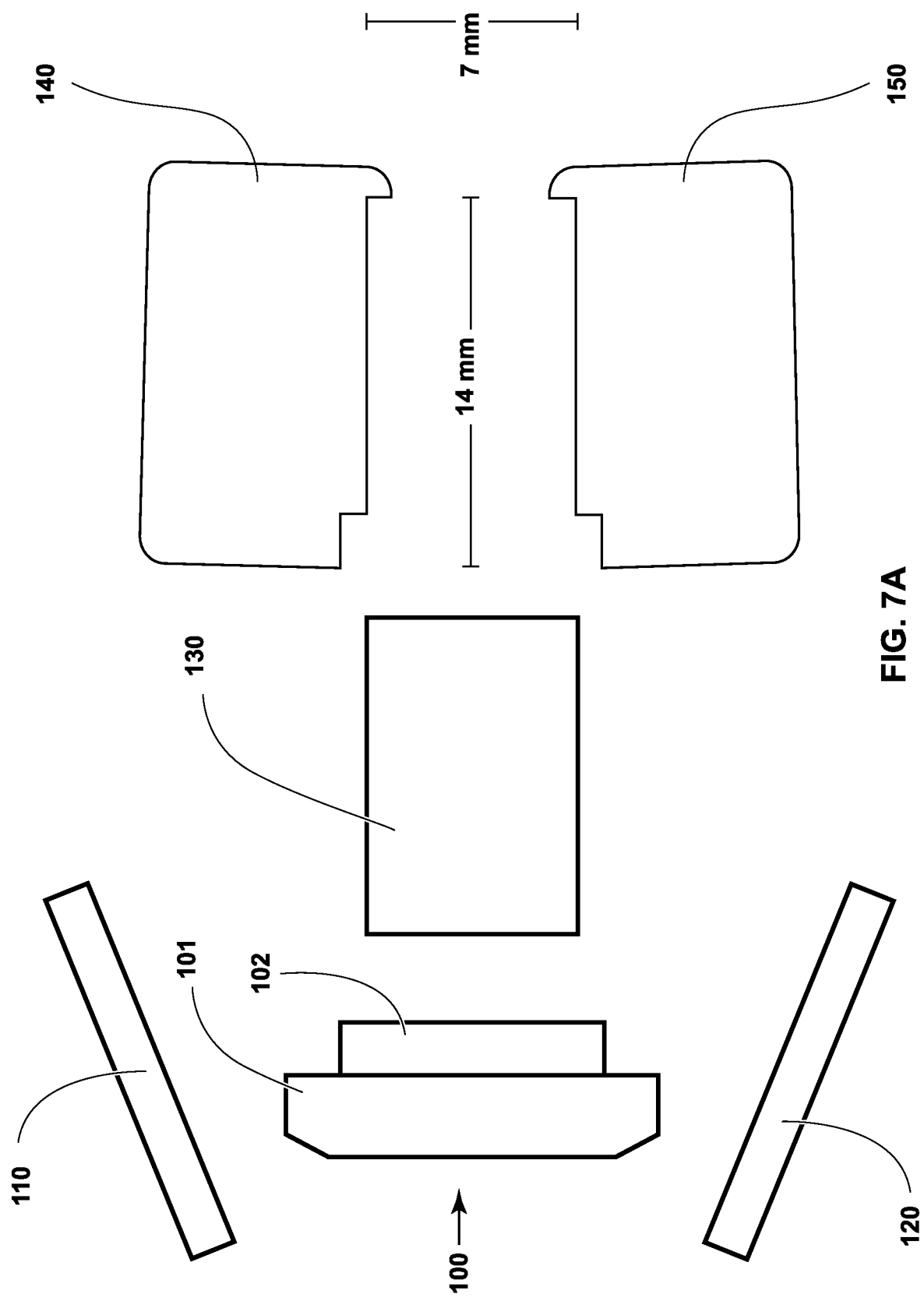
FIGS. 7A-E are exploded views of a fusion apparatus according to an exemplary embodiment as the apparatus is affixed to the vertebrae.

FIGS. 7A through 7E illustrate exploded views of the apparatus according to an exemplary embodiment as the apparatus is affixed to the vertebrae. Referring to FIG. 7A, a channel has been carved between vertebrae 140 and 150. The channel may have a major diameter to accommodate plate 100 and a minor diameter to accommodate graft 130. According to an exemplary embodiment, the minor diameter may be 7 mm in the cephalo-caudal direction, and the major diameter may be approximately 10 mm in the cephalo-caudal direction. The channel may have a depth of 14 mm in the anterior-posterior direction. In the exemplary embodiment, plate 100 may be a solid component including an anterior portion 101 and a posterior portion 102. The cephalo-caudal height of anterior portion 101 may be greater than the cephalo-caudal height of posterior portion 102.

Figure 7B:
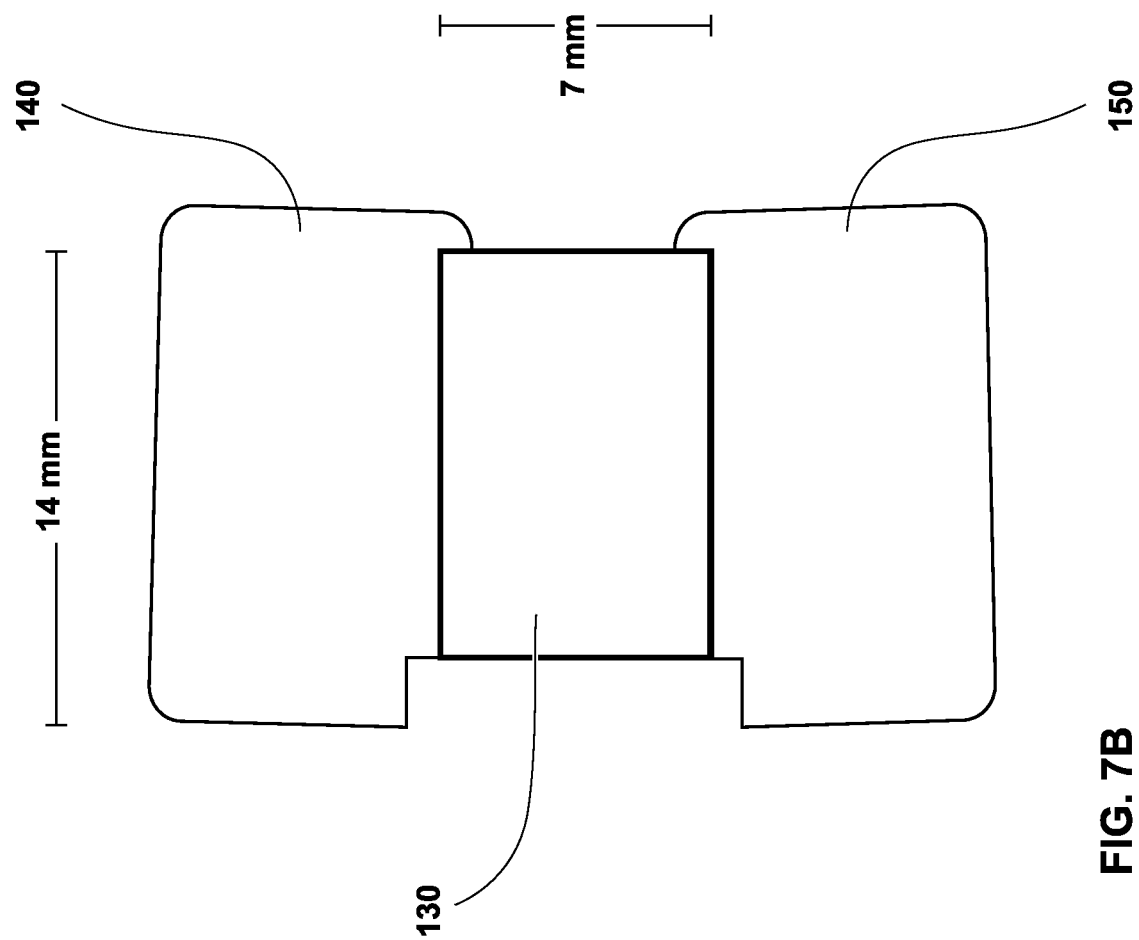
Figure 7B:
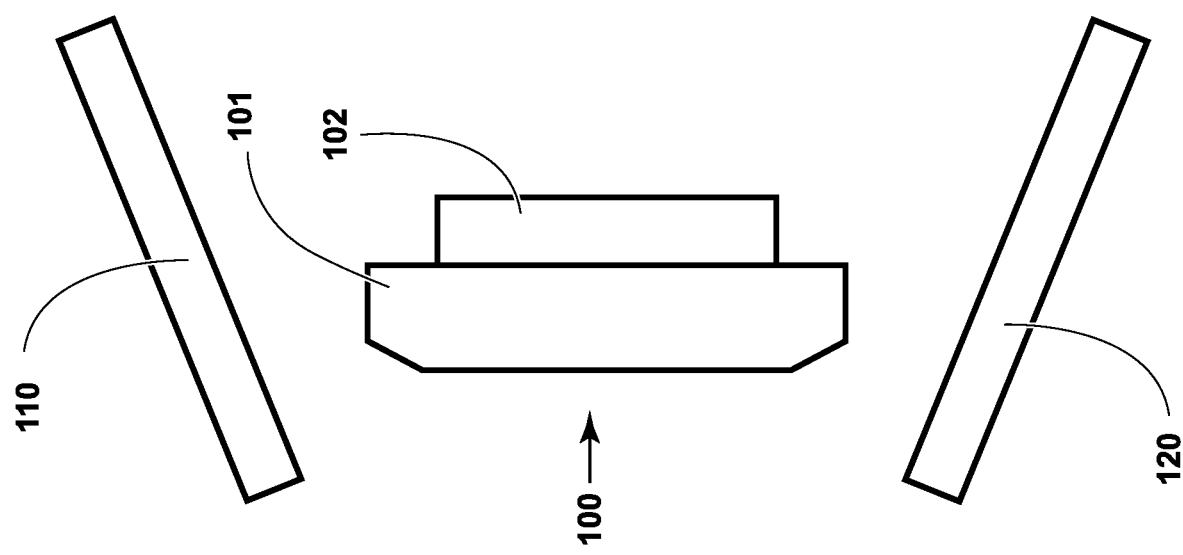

In FIG. 7B, the graft 130 has been inserted into the minor diameter of the channel. The graft 130 may extend from an anterior end of the minor-diameter channel to a posterior end of the minor-diameter channel.

Figure 7C:
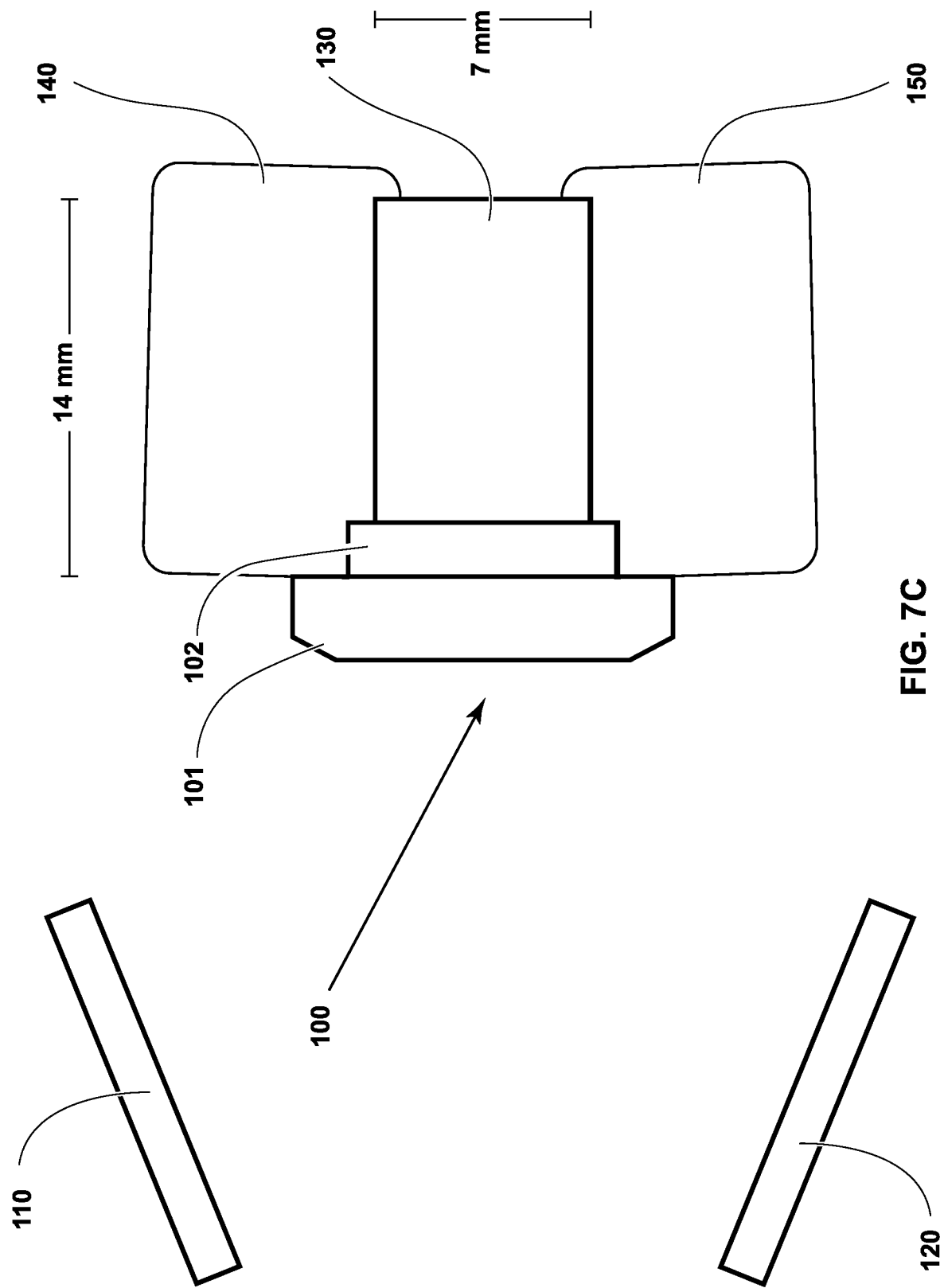

In FIG. 7C, plate 100 has been disposed so that the posterior portion 102 fits within the major-diameter portion of the channel and the anterior portion 101 resides on the anterior surface of vertebrae 140 and 150. Posterior portion 102 may abut the anterior end of graft 130.

Figure 7D:
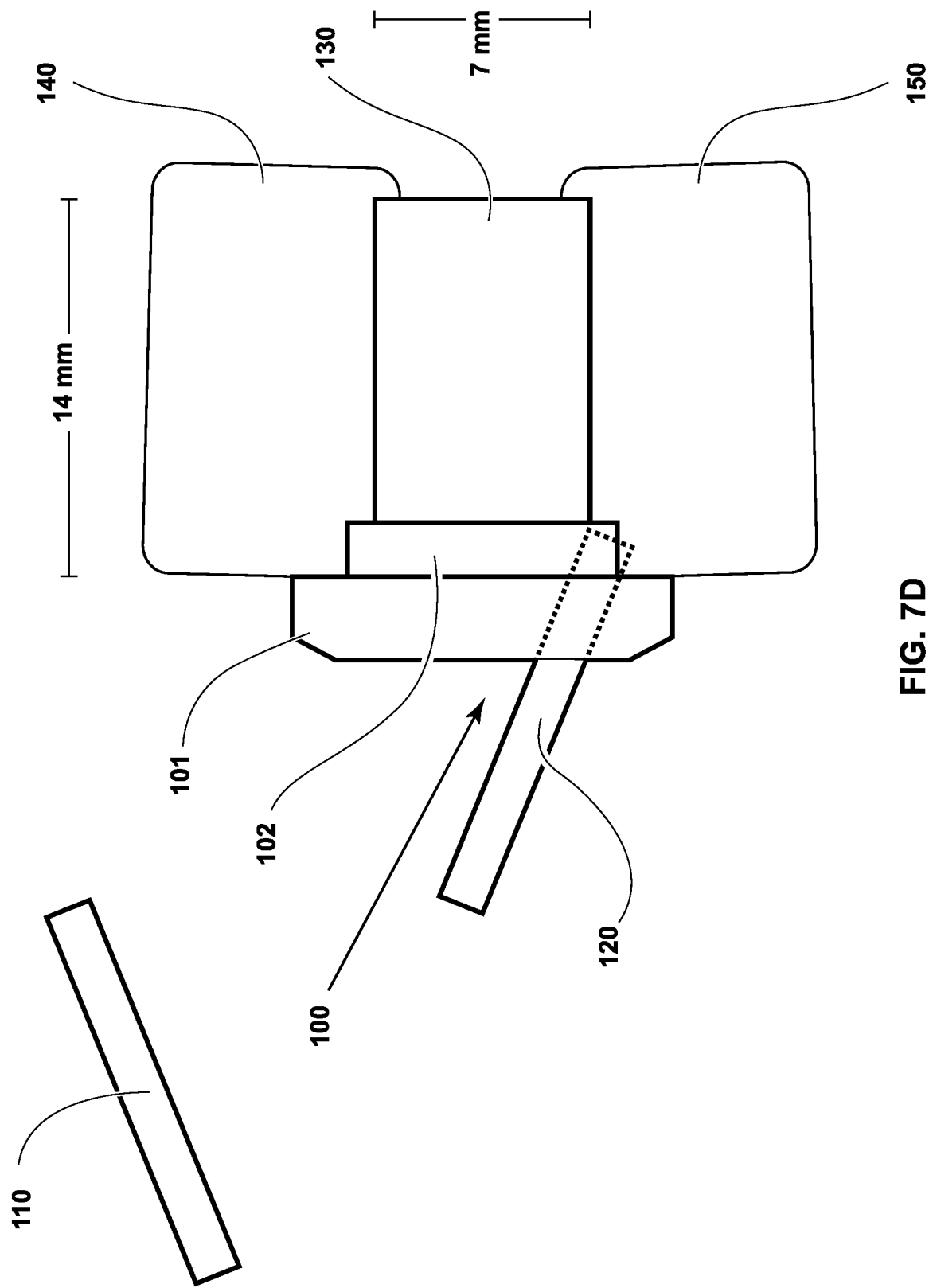

In FIG. 7D, screw 120 is positioned so as to be inserted through plate 100 into vertebrate 150. Screw 120 may be inserted into vertebrate 150 at an angle between the cephalo-caudal direction and the anterior-posterior direction. Because anterior portion 101 of plate 100 is located on the anterior surface of vertebrae 140 and 150, screw 120 is easier to insert, as compared with inserting a screw into a plate that is disposed entirely within the space between vertebrae 140 and 150. In addition, because the posterior portion 102 is disposed within the channel between vertebrae 140 and 150, plate 100 may have a lesser cephalo-caudal height as compared to a plate disposed entirely on the anterior surface of vertebrae 140 and 150. The configuration shown in FIG. 7D allows for angled screw insertion, which reduces the possibility that the screw 120 will pullout as compared to screws inserted in the anterior-posterior direction.

Figure 7E:
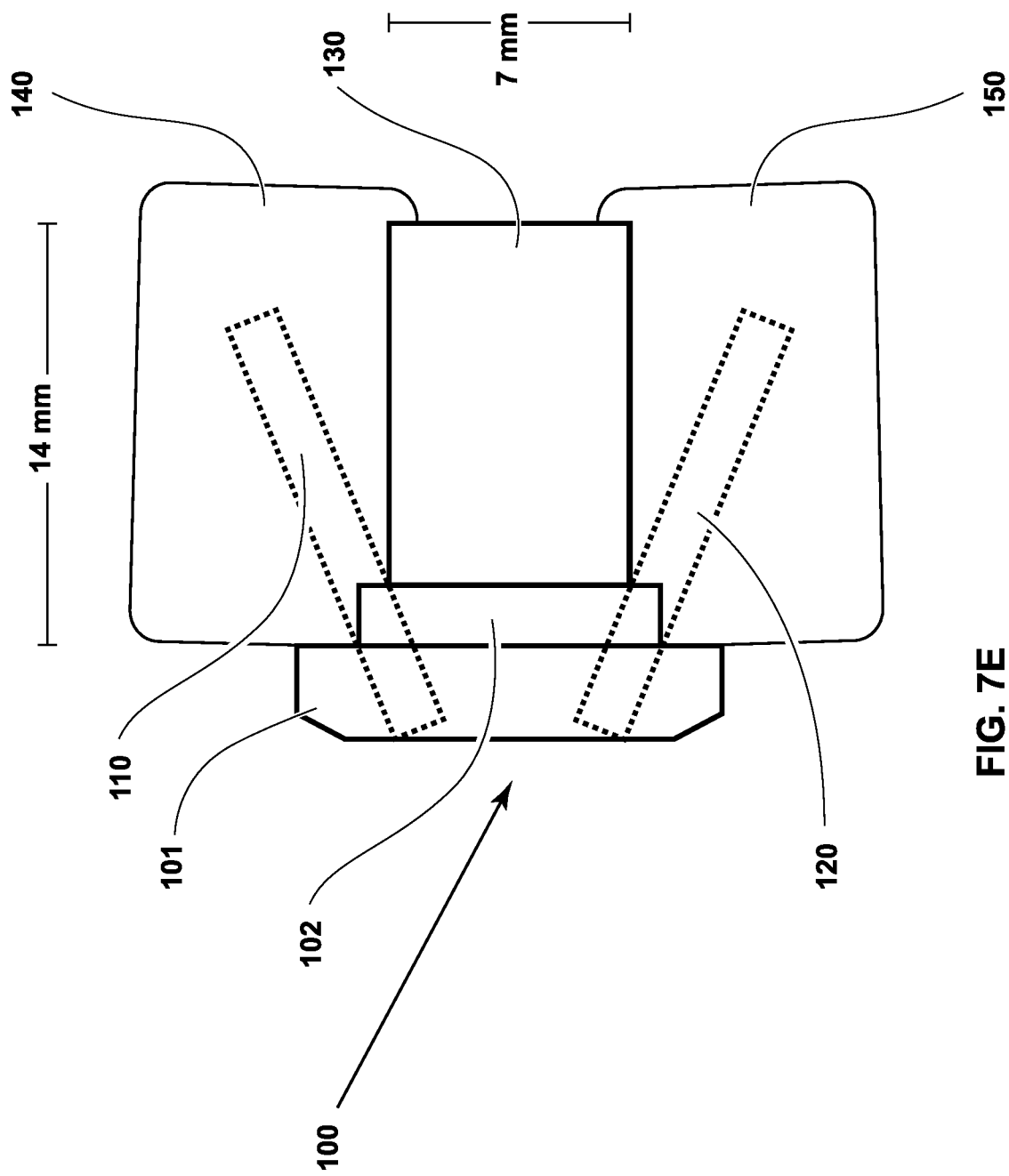

In FIG. 7E, both screws 110 and 120 are inserted at an angle into vertebrae 140 and 150, respectively. Although only two screws are shown in FIGS. 7A-E, one of ordinary skill in the art would understand that additional screws may be used.

Figure 8B:
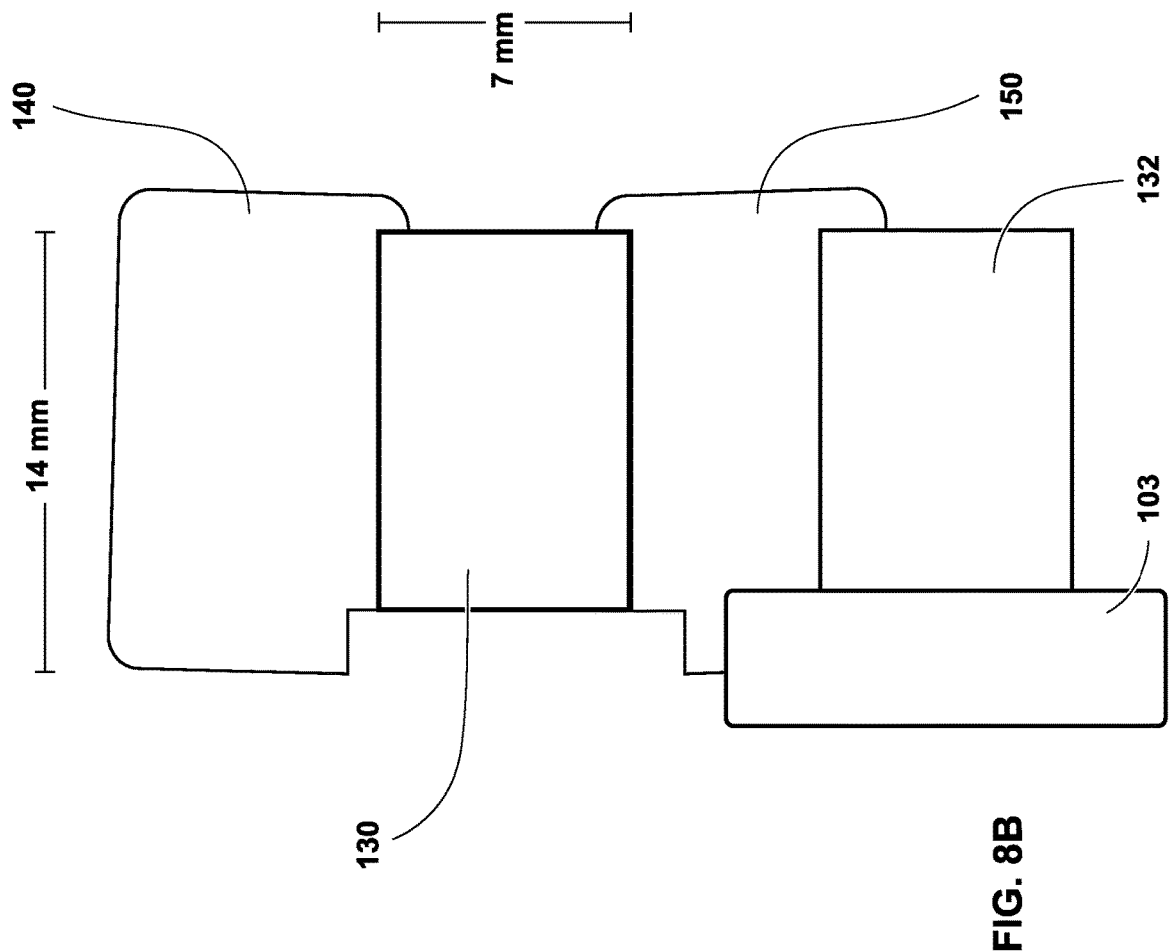
Figure 8B:
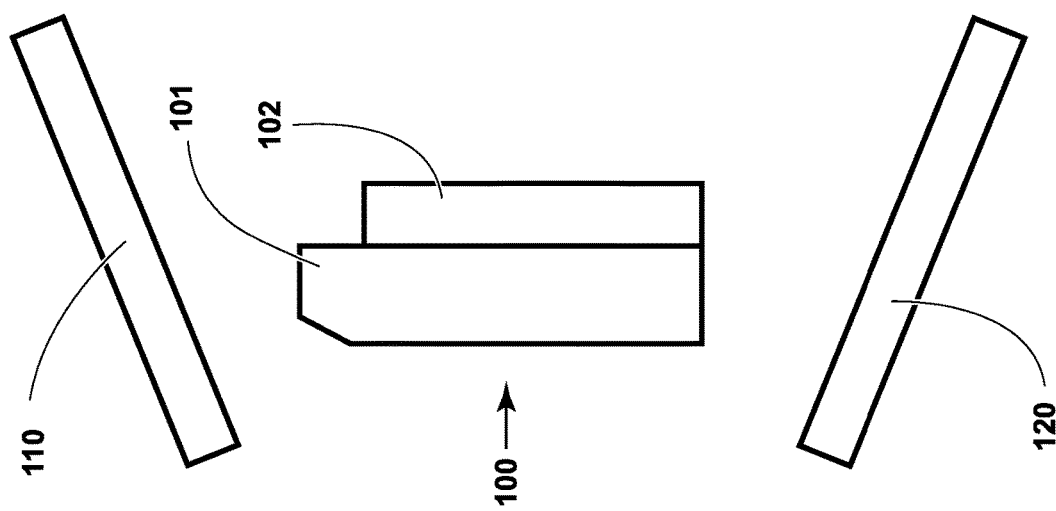

FIGS. 8A through 8E illustrate exploded views of the apparatus according to another exemplary embodiment as the apparatus is affixed to the vertebrae. Referring to FIG. 8A, a pre-existing plate 103 has been previously affixed to vertebrate 150 in order to secure bone graft 132 within the disc space below vertebrate 150 in the caudal direction. Because of the close proximity of pre-existing plate 103 to the channel between vertebrae 140 and 150, it may not be possible to use the plate 100 shown in FIGS. 7A-7E because plate 100 and pre-existing plate 103 may interfere with each other. However, in certain cases of revision, add-on, or adjacent segment disease (ASD, also called adjacent segment pathology, ASP), it may be beneficial to not remove pre-existing plate 103. A zero-profile plate could be used in order to avoid interfering with pre-existing plate 103, however, zero-profile plates may not achieve proper fusion in this case.

Figure 8C:
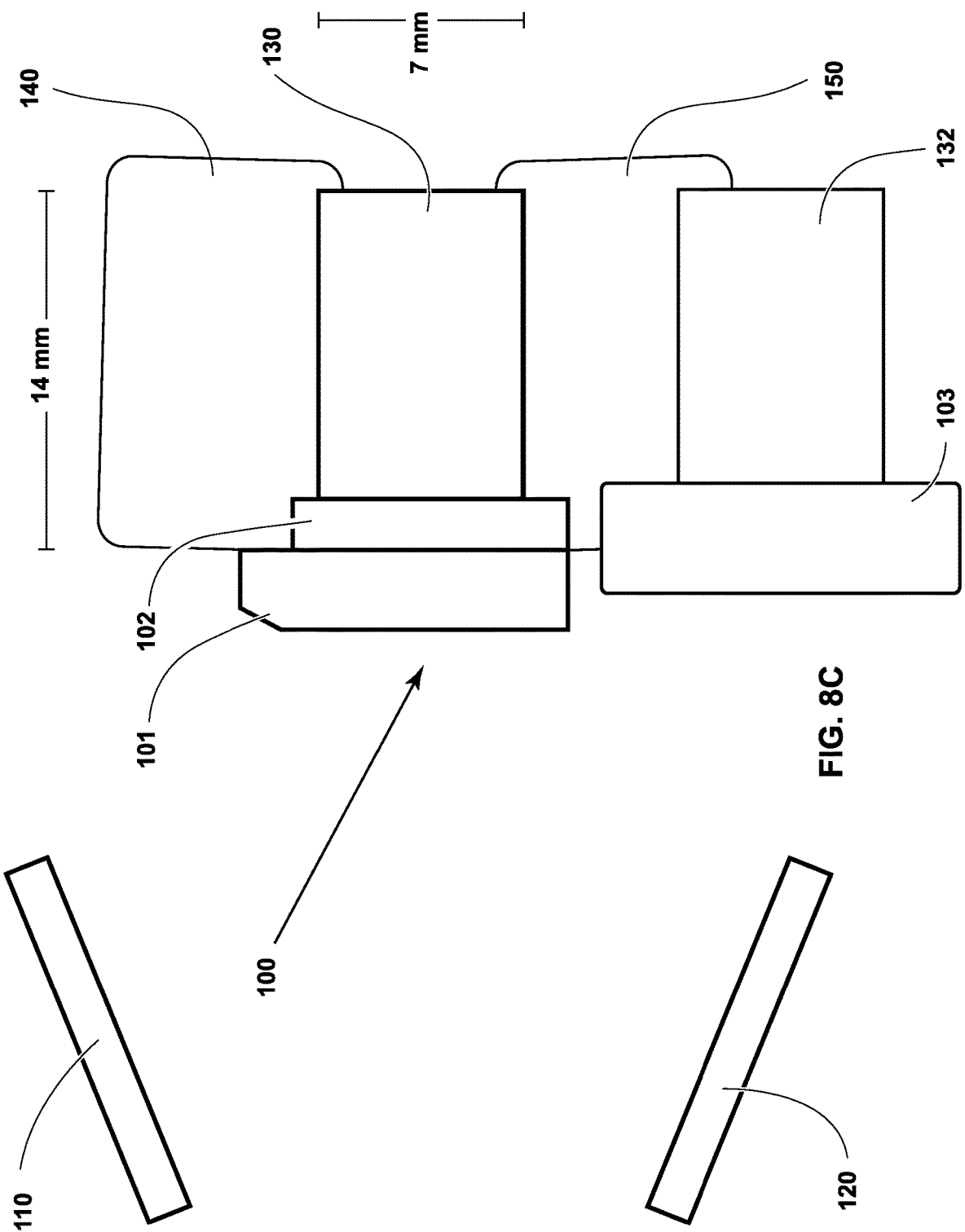

Accordingly, as shown in FIG. 8A, a modified version of plate 100 may be used in which an anterior portion of the plate does not extend beyond the major diameter of the channel in the cephalo-caudal direction. As shown in FIGS. 8B and 8C, graft 130 is inserted into the channel between vertebrae 140 and 150. More specifically, graft 130 is inserted into the minor diameter or posterior portion of the channel. In FIG. 8C, plate 100 is inserted into the major diameter or anterior portion of the channel such that a cephalad end of the plate 100 extends beyond the major diameter of the channel in the cephalad direction. The caudal end of plate 100 does not extend beyond the major diameter of the channel in order to avoid interfering with pre-existing plate 103.

Figure 8D:
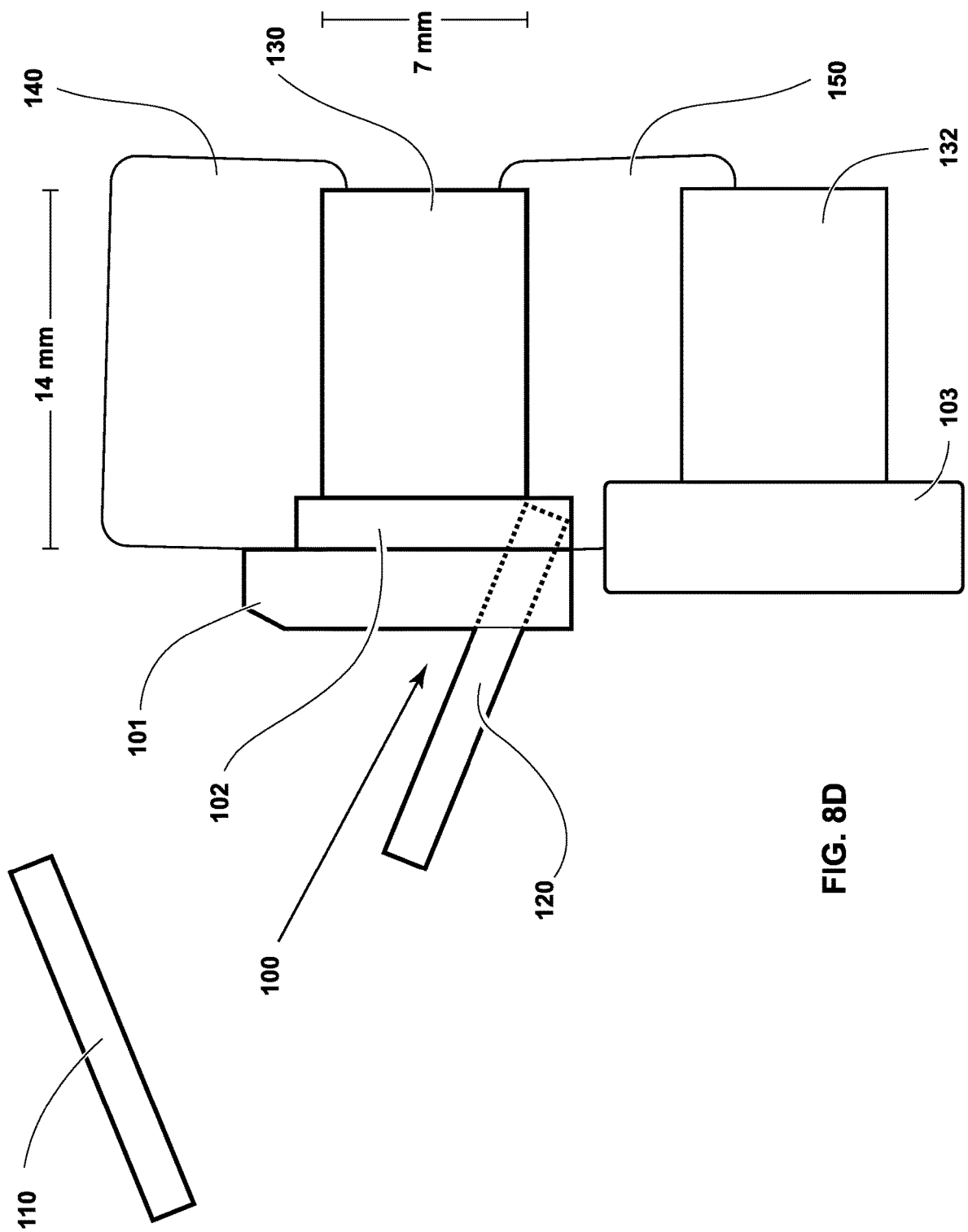
Figure 8E:
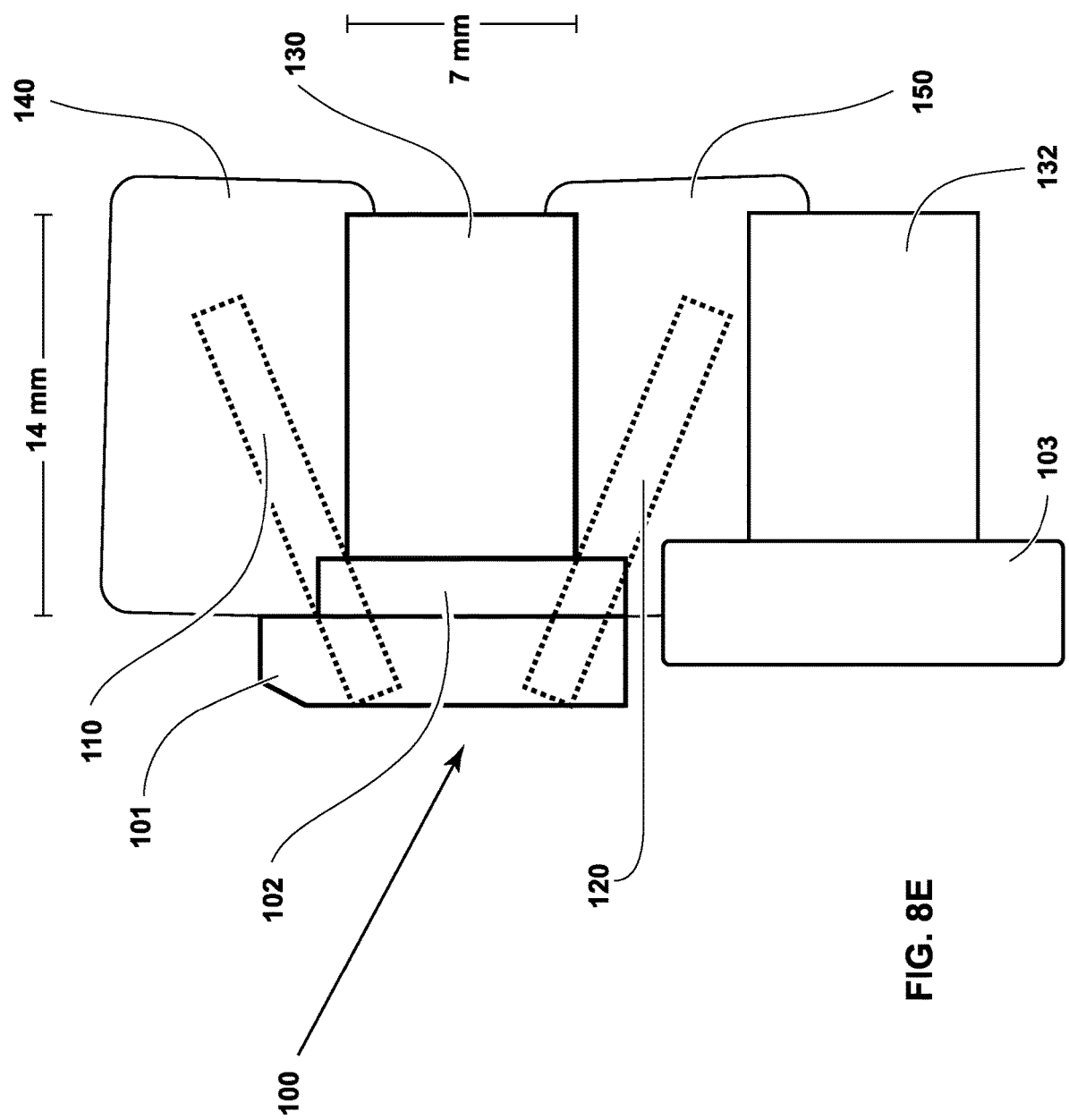

In FIG. 8D, screw 120 is positioned so as to be inserted through plate 100 into vertebrate 150. Screw 120 may be inserted near the caudal end of plate 100, which does not extend beyond the major diameter of the channel. In FIG. 8E, both screws 110 and 120 are inserted into vertebrae 140 and 150, respectively, to secure plate 100.

Although a few exemplary embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A method of surgery comprising:
   preparing a space between adjacent vertebral bodies;
   placing a body in the space, the body being made of PEEK; and
   affixing a plate, which is separate from the body, to the adjacent vertebral bodies such that a posterior portion of the plate is disposed within the space, and an anterior portion of the plate engages anterior portions of the adjacent vertebral bodies, the plate being made of a metal material.

2. The method according to claim 1, wherein preparing the space includes defining a channel including a posterior part and an anterior part, wherein a cephalo-caudal height of the anterior part is greater than a cephalo-caudal height of the posterior part.

3. The method according to claim 2, wherein affixing the plate includes affixing the plate such that a first cephalo-caudal end of the anterior portion of the plate is disposed at least approximately 5 mm from a disc adjacent the first cephalocaudal end in a cephalo-caudal direction.

4. The method according to claim 1, wherein placing the body in the space includes placing a graft in the space.

5. The method according to claim 1, wherein placing the body includes placing at least a portion of the body approximately 11 mm to approximately 14 mm away from anterior surfaces of the adjacent vertebral bodies.

6. The method according to claim 1, wherein affixing the plate includes affixing a plate having a posterior portion having a cephalo-caudal height of about 6 to 8 mm.

7. The method according to claim 1, wherein affixing the plate includes inserting a screw through the plate at an acute angle with respect to an anterior surface of the plate.

8. The method according to claim 1, wherein affixing the plate includes inserting screws through respective bores defined in the plate such that the screws are received in a first vertebral body of the adjacent vertebral bodies.

9. The method according to claim 1, wherein the anterior portion of the plate is separate from and connectable to the posterior portion of the plate, the anterior portion of the plate defines recesses and the posterior portion of the plate includes anterior protrusions configured to be received in the recesses of the anterior portion and a posterior protrusion configured to extend into a recess of the body.

10. The method according to claim 9, wherein the anterior protrusions are hollow and configured to receive screws to affix the plate to the adjacent vertebral bodies.

11. The method of claim 1, wherein the affixing step includes abutting an anterior end of the body with the posterior portion of the plate.

12. The method of claim 1, further comprising connecting the body and the plate via a threaded member.

13. A method of surgery comprising:
   preparing a space between adjacent vertebral bodies;
   placing an implant body of a first material into the space, the first material being PEEK;
   engaging a plate of a second material to the vertebral bodies so that a first portion of the plate contacts outer surfaces of the vertebral bodies and a second portion of the plate is positioned within the space adjacent to the implant body, the second material being a metal material; and inserting bone screws through the first portion of the plate and into the vertebral bodies to secure the plate thereto.

14. The method of claim 13, wherein the placing and engaging steps are performed sequentially.

15. The method of claim 13, wherein the body is a cage filled with allograft bone.

16. The method of claim 13, further comprising cutting the vertebral bodies within the disc space in order to form a channel within the disc space for receipt of the second portion of the plate.

17. The method of claim 13, wherein the first material is a metal material, and the second material is a polymer material.

* * * * *